US012679795B2

(12) United States Patent
Xu et al.

(10) Patent No.: US 12,679,795 B2
(45) Date of Patent: Jul. 14, 2026

(54) PRODUCTION OF ACROLEIN OR ACRYLIC ACID FROM ISO-PROPANOL WITH HIGH YEILD AND LOW COST

(71) Applicant: Rohm and Haas Company, Collegeville, PA (US)

(72) Inventors: Jinsuo Xu, Berwyn, PA (US); Daniel A. Bors, Maple Glen, PA (US)

(73) Assignee: ROHM AND HAAS COMPANY, Collegeville, PA (US)

( * ) Notice: Subject to any disclaimer, the term of this patent is extended or adjusted under 35 U.S.C. 154(b) by 478 days.

(21) Appl. No.: 18/547,716

(22) PCT Filed: Mar. 2, 2022

(86) PCT No.: PCT/US2022/018413
§ 371 (c)(1),
(2) Date: Aug. 24, 2023

(87) PCT Pub. No.: WO2022/187291
PCT Pub. Date: Sep. 9, 2022

(65) Prior Publication Data
US 2024/0132433 A1 Apr. 25, 2024
US 2024/0228417 A9 Jul. 11, 2024

Related U.S. Application Data

(60) Provisional application No. 63/156,453, filed on Mar. 4, 2021.

(51) Int. Cl.
| | |
|---|---|
| *C07C 45/38* | (2006.01) |
| *B01J 23/00* | (2006.01) |
| *B01J 23/28* | (2006.01) |
| *B01J 23/31* | (2006.01) |
| *C07C 51/25* | (2006.01) |
| *C07C 51/44* | (2006.01) |

(52) U.S. Cl.
CPC ............. *C07C 45/38* (2013.01); *B01J 23/002* (2013.01); *B01J 23/28* (2013.01); *B01J 23/31* (2013.01); *C07C 51/252* (2013.01); *C07C*

*51/44* (2013.01); *B01J 2523/17* (2013.01); *B01J 2523/51* (2013.01); *B01J 2523/53* (2013.01); *B01J 2523/69* (2013.01); *B01J 2523/842* (2013.01); *B01J 2523/845* (2013.01); *B01J 2523/847* (2013.01)

(58) Field of Classification Search
CPC ......... C07C 45/38; C07C 47/22; C07C 57/04; C07C 51/252; B01J 23/28; B01J 23/31
See application file for complete search history.

(56) References Cited

U.S. PATENT DOCUMENTS

| | | | | |
|---|---|---|---|---|
| 3,736,354 | A * | 5/1973 | Yanagita | ............... C07C 51/252 502/308 |
| 4,208,306 | A * | 6/1980 | Childress | ............. B01J 23/8878 502/309 |
| 9,296,676 | B2 * | 3/2016 | Devaux | ................. C07C 253/18 |
| 12,565,464 | B2 | 3/2026 | Xu | |
| 2004/0063998 | A1 | 4/2004 | Hirao et al. | |
| 2011/0301316 | A1 | 12/2011 | Dubois et al. | |
| 2018/0215696 | A1 | 8/2018 | Paul et al. | |

FOREIGN PATENT DOCUMENTS

| | | | | |
|---|---|---|---|---|
| JP | 2015160807 | | 9/2015 | |
| JP | 2015160807 A | * | 9/2015 | ............. C07C 45/38 |

* cited by examiner

*Primary Examiner* — Yate' K Cutliff
(74) *Attorney, Agent, or Firm* — CANTOR COLBURN LLP

(57) ABSTRACT

Acrolein is produced by selectively oxidizing iso-propanol over a first mixed metal oxide catalyst in the presence of oxygen in the vapor phase. The first mixed metal oxide catalyst comprises oxides of molybdenum and bismuth. Acrylic acid is produced by selectively oxidizing the acrolein over a second mixed metal oxide catalyst in the presence of oxygen in the vapor phase. The second mixed metal oxide catalyst has a different composition from the first mixed metal oxide catalyst.

11 Claims, No Drawings

PRODUCTION OF ACROLEIN OR ACRYLIC ACID FROM ISO-PROPANOL WITH HIGH YEILD AND LOW COST

FIELD OF THE INVENTION

The present invention relates to a process for the selective oxidization of iso-propanol to produce acrolein, and further, the selective oxidization of the produced acrolein to produce acrylic acid.

BACKGROUND OF THE INVENTION

Various processes for preparing acrylic acid are known in the art. Most commercial acrylic acid is produced using fossil fuel based feedstock, such as, for example, propylene.

Most commercial iso-propanol is produced via hydration of propylene derived from fossil fuels or hydrogenation of acetone, which is a byproduct of phenol production. A small portion of acetone is made from carbohydrates such as starch and glucose via traditional acetone-butanol-ethanol (ABE) fermentation processes. Therefore, it is more economically feasible to produce acrylic acid directly from propylene.

Due to growing demand for bio-derived carbon in chemical products, there is growing research activities in improving the efficacy for on-purpose production of iso-propanol from nonfood biomass such as sugar cane or agricultural crop residue. There remains a need, however, for methods of producing acrolein and/or acrylic acid from biomass-derived feedstocks.

SUMMARY OF THE INVENTION

The present invention is directed to methods for preparing acrolein from iso-propanol, and further, to produce acrylic acid from the acrolein.

According to one aspect of the present invention, a method comprises selectively oxidizing isopropanol over a first mixed metal oxide catalyst in the presence of oxygen in the vapor phase to produce acrolein, wherein the first mixed metal oxide catalyst comprises oxides of molybdenum and bismuth.

Another aspect of the present invention comprises further selectively oxidizing the acrolein over a second mixed metal oxide catalyst in the presence of oxygen in the vapor phase, wherein the second mixed metal oxide catalyst has a different composition from the first mixed metal oxide catalyst.

DETAILED DESCRIPTION OF EMBODIMENTS OF THE INVENTION

As used herein, the terms "a," "an," "the," "at least one," and "one or more" are used interchangeably. The terms "comprises," "includes," "contains," and variations thereof do not have a limiting meaning where these terms appear in the description and claims. Thus, for example, a mixture that includes a polymerization inhibitor can be interpreted to mean that the mixture comprises at least one polymerization inhibitor.

As used herein, recitations of numerical ranges by endpoints includes all numbers subsumed in that range (e.g. 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.1 to 100, from 1 to 99.99, from 1.01 to 99.99, from 40 to 6, from 1 to 55, etc.

As used herein, the recitations of numerical ranges and/or numerical values, including such recitations in the claims, can be read to include the term "about." In such instances, the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety or its equivalent U.S. version is so incorporated by reference) especially with respect to the disclosure of definitions (to the extent not inconsistent with any definitions specifically provided in this disclosure) and general knowledge in the art.

One aspect of the present invention relates to a method for producing acrolein from iso-propanol.

In the inventive process, iso-propanol is selectively oxidized over a first mixed metal oxide catalyst in the presence of oxygen in the vapor phase.

The first mixed metal oxide catalyst is a solid catalyst comprising oxides of molybdenum (Mo) and bismuth (Bi). The first mixed metal oxide catalyst may also contain at least one additional element selected from iron (Fe), cobalt (Co), nickel (Ni), or combinations thereof. When the first mixed metal oxide catalyst contains at least one additional element, the molybdenum and bismuth are the main metal elements present. Preferably, the first mixed metal oxide catalyst comprises at least 40 wt. % of molybdenum and bismuth based on the total weight of metals in the first mixed metal oxide catalyst, such as, for example, at least 50 wt. %, at least 60 wt. %, or at least 70 wt. %.

The first mixed metal oxide catalyst can be any commercially available catalyst used in the oxidation of propylene to acrolein.

The yield of acrolein based on the iso-propanol feed is preferably greater than 60% and the mass ratio of propionic acid, a byproduct of the reaction, to acrolein is preferably less than 0.002.

Acetone can be formed as a by-product of the iso-propanol to acrolein oxidation reaction. To reduce the amount of acetone formed, the oxygen level in the first reactor may be increased. Alternatively, the reactor temperature may be adjusted to favor acrolein production.

Another aspect of the present invention relates to the production of acrylic acid from iso-propanol. The inventive process for producing acrylic acid from iso-propanol is a two-step process. In a first step, iso-propanol is selectively oxidized over a first mixed metal oxide catalyst to form acrolein, as described above.

In a second step, the acrolein is then selectively oxidized over a second mixed metal oxide catalyst in the presence of oxygen in the vapor phase, wherein the second mixed metal oxide catalyst has a different composition from the first mixed metal oxide catalyst.

The second mixed metal oxide catalyst is a solid catalyst that comprises oxides of molybdenum (Mo) and vanadium (V). The second mixed metal oxide catalyst may also contain at least one additional element selected from tungsten (W), copper (Cu), iron (Fe), antimony (Sb), and phosphorus (P). When the second mixed metal oxide catalyst contains at least one additional element, the molybdenum and vanadium are the main metal elements present. Preferably, the second mixed metal oxide catalyst comprises at least 40 wt. % of molybdenum and vanadium based on the total weight of metals in the second mixed metal oxide catalyst, such as, for example, at least 50 wt. %, at least 60 wt. %, or at least 70 wt. %.

The second mixed metal oxide catalyst can be any commercially available mixed metal oxide catalyst used for oxidation of acrolein to acrylic acid.

The yield of acrylic acid based on the iso-propanol feed is preferably greater than 70%, and the mass ratio of propionic acid, a byproduct of the reaction, to acrylic acid is preferably less than 0.001.

In the selective oxidation reaction to form acrolein and/or acrylic acid, the oxygen can be present in the form of purified oxygen, oxygen in air, or lattice oxygen of the mixed metal oxide catalyst. Preferably, the oxygen is from air or the lattice oxygen of the mixed metal oxide catalyst.

In either the selective oxidation of iso-propanol to produce acrolein or the selective oxidation of acrolein to produce acrylic acid, steam may be added to assist the reaction.

Purification of the acrolein and/or acrylic acid can be achieved by one or more techniques known in the art, such as, for example, absorption using water or an organic solvent, extraction, fractional distillation, or melt crystallization.

Preferably, the iso-propanol is produced from a biomass derived feedstock. For example, iso-propanol can be produced via biofermentation. For example, iso-propanol can be formed by iso-propanol-butanol-ethanol (IBE) fermentation.

All living organisms, plant and animal alike, contain a certain amount of carbon-14 ($^{14}$C), which is produced in the atmosphere and fixed by plants during photosynthesis. The ratio of $^{14}$C to $^{12}$C ranges from 1 to $1.5 \times 10^{-12}$. Carbon-14 is a radioactive material having a half-life of around 5700 years. Therefore, biomass derived feedstock contains a ratio of $^{14}$C to $^{12}$C similar to that of living organisms, i.e., around 1 to $1.5 \times 10^{-12}$.

Preferably, the acrolein and/or acrylic acid produced by the process of the present invention comprises a ratio of $^{14}$C:$^{12}$C of at least $0.5 \times 10^{-13}$. More preferably, the acrolein and/or acrylic acid produced by the process of the present invention comprises a ratio of $^{14}$C:$^{12}$C of at least $0.75 \times 10^{-13}$. Even more preferably, the acrolein and/or acrylic acid produced by the process of the present invention comprises a ratio of $^{14}$C:$^{12}$C of at least $0.8 \times 10^{-13}$. Most preferably, the feedstock used in the process of the present invention is entirely sourced from biomass derived material and the ratio of $^{14}$C to $^{12}$C is the same as that found in nature, i.e., about 1 to $1.5 \times 10^{-12}$.

EXAMPLES

The following examples illustrates the present invention but are not intended to limit the scope of the invention.

I. Inventive Example—Oxidation of Iso-Propanol to Acrolein

Iso-propanol was oxidized mainly to acrolein in first-stage reactor to produce acrylic acid. The catalyst used in the first stage reactor is Mo- and Bi-based mixed oxide catalyst, abbreviated as R1 catalyst. In this example 10 ml of a Mo- and Bi-based R1 catalyst from Nippon Kayaku Co. (Tokyo, Japan) was loaded into a ½" (1.27 cm) outer diameter (OD) stainless steel (SS) first stage tube reactor heated in fluidized sand bath furnace. The reactor was heated in flowing gas mixture of air 171.80 sccm and N2 38.2 sccm to the desired reactor temperature, then a mixture of liquid containing iso-propanol and D.I. was injected at rate of 3.22 g/h iso-propanol and water 0.96 g/h The product mixture out of the 1st stage reactor, abbreviated as R1-Exit, was collected and analyzed. The R1-Exit first flew through Trap 1 which was a 100-500 ml stainless vessel wrapped with ¼" (0.635 cm) copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4 hours. An inhibitor solution of 6-12 grams was injected to Trap 2, Trap 3A and 3B before sample collection to prevent polymer formation. Trap 2 collected very little material most times. 0.2 wt. % of hydroquinone in ethanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (DB-FFAP 123-3232E). The conversions of propylene, mass balance of carbon, yields of major products or byproducts such as acrylic acid, acrolein, acetaldehyde, propionaldehyde, propionic acid, acetic acid, $CO_x$ (CO and $CO_2$) are calculated using the formula below:

Iso-propanol conversion (%)=(moles of iso-propanol fed−moles of iso-propanol in R1-Exit)/moles of iso-propanol fed.

Carbon mass balance (%)=(total amount of carbon from molecules in R1-Exit including $CO_2$, CO, propylene, acetaldehyde, acrolein, acetic acid, propionic acid, acrylic acid)/(total amount of carbon from iso-propanol fed)*100.

The yields of acrolein, acetaldehyde, and acrylic acid, and carbon mass balance after the $2^{nd}$ stage reactor were calculated using the formula below:

Yield of product (%)=(moles of the product in R1-Exit)/moles of iso-propanol fed*100

The test was conducted with two different reactor bath temperatures (327 and 347° C.). In Example 1, the bath temperature was 327° C. and the peak bed temperature was 330° C., providing a conversion of 99.3% and a carbon mass balance of 104.3%. In Example 2, the bath temperature was 347° C. and the peak bed temperature was 358° C., providing a conversion of 100% and a carbon mass balance of 111.1%. The results are listed in the Table 1. With almost complete conversion of iso-propanol, the yield of acrolein reached 63.7%.

TABLE 1

| | | | | Product Yield (%) | | | | |
|---|---|---|---|---|---|---|---|---|
| | $CO_x$ | Ald | Ace | PP | Acro | Allyl | HAc | PA | AA |
| Ex. 1 | 3.78 | 2.33 | 19.7 | 22.4 | 54.3 | 0.802 | 0.681 | 0.047 | 0.248 |
| Ex. 2 | 9.28 | 7.40 | 18.1 | 6.06 | 63.7 | 0.228 | 4.10 | 0.079 | 2.44 |

$CO_x = CO + CO_2$;
Ald = acetaldehyde;
Ace = acetone;
PP = propylene;
Acro = acrolein;
Allyl = allyl alcohol;
HAc = acetic acid;
PA = propionic acid;
AA = acrylic acid

II. Comparative Example—Oxidation of Iso-Propanol in One Step Over Mo, V-Based Oxide Catalyst Iso-propanol oxidation was conducted in one step over a Mo, V-based oxide catalyst. The experiment was similar to Example 1 except the isopropanol was oxidized directly over commercial catalyst from NK containing Mo and V as main ingredients.

Comparative Example 1 was performed at a bath temperature of 320° C. and a peak bed temperature of 319° C., providing a conversion of 100% and a carbon mass balance of 93.5%. Comparative Example 2 was performed at a bath temperature of 330° C. and a peak bed temperature of 333° C., providing a conversion of 100% and a carbon mass balance of 89.9%. In the Comparative Examples, the main product was propylene and the yield of acrylic acid was less than 10%. The mass ratio of PA/AA was 0.046, which was ~50 times higher than Example 1.

TABLE 2

| | | | | Product Yield (%) | | | | |
|---|---|---|---|---|---|---|---|---|
| | $CO_x$ | Ald | Ace | PP | Acro | Allyl | HAc | PA | AA |
| C.E. 1 | 5.19 | 0.16 | 8.92 | 68.7 | 0.82 | 0.01 | 4.87 | 0.32 | 4.57 |
| C.E. 2 | 8.22 | 0.17 | 4.92 | 61.6 | 0.82 | 0.01 | 7.15 | 0.31 | 6.72 |

III. Inventive Example—Oxidation of Iso-Propanol to Acrylic Acid

Iso-propanol oxidation to acrylic acid was conducted in two stages. First iso-propanol was oxidized mainly to acrolein in first-stage reactor, in this case a tubular reactor. The catalyst used in the first stage reactor is Mo- and Bi-based mixed oxide catalyst, abbreviated as R1 catalyst. In this example 10 ml of a Mo- and Bi-based R1 catalyst from Nippon Kayaku Co. (Tokyo, Japan) was mixed with 10 ml of ⅛" (0.32 cm) Denstone™ 57 beads (Saint-Gobain Norpro, Stow, OH), before being loaded into a 2.54 cm (1") outer diameter (OD) stainless steel (SS) first stage tube reactor (0.834" (2.11 cm) ID).

The product mixture out of the 1st stage reactor, abbreviated as R1-Exit, was sent the $2^{nd}$ stage reactor in ¼" (0.635 cm) SS tube heated by electrical heating tape. The skin temperature was controlled around 170±10° C.

The $2^{nd}$-stage reactor contains Mo, V-based mixed oxide catalyst, abbreviated as R2 catalyst. In this example 10 ml of a Mo- and V-based commercial R2 catalyst was loaded into the feed inlet side of a U-shaped SS tube with ½" (1.27 cm) OD. The other internal space of the U-shaped tube was filled with Denstone™ beads. The U-shaped tube was put into a fluidized sand bath furnace with the catalyst bed section immersed in the sand bath. The air was used to fluidize the sand at flow rate of 3.3-3.5 SCFM (standard cubic feet per minute) (0.093-0.099 m³/min). The temperature difference in the bath was controlled no more than 3° C. by maintaining high air flow rate. The bath temperature was adjusted to achieve desired conversion of acrolein to acrylic acid. The effluent from the $2^{nd}$ stage reactor was designated as R2-Exit.

The first stage reactor tube was first heated to 305° C. or higher in a clam-shell electrical furnace in flowing gas mixture of air 171.80 sccm and N2 38.2 sccm. The second stage reactor was heated to 270° C. The values of all gas flow rates were under standard temperature (0° C.) and standard pressure (101.3 kPa) conditions. The iso-propanol was mixed D.I. water (78.0 wt % of iso-propanol) and injected into a SS mixer vessel at rate of 0.073 ml/min when the reactor reached the desired temperature. The SS mixer vessel was heated to 160-170° C. with the feed air/nitrogen carrying the vapor into the reactor.

The R2-Exit was collected and analyzed. The R2-Exit first flew through Trap 1 which was a 100-500 ml stainless vessel wrapped with ¼" (0.635 cm) copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4 hours. An inhibitor solution of 6-12 grams was injected to Trap 2, Trap 3A and 3B before sample collection to prevent polymer formation. Trap 2 collected very little material most times. 0.2 wt. % of hydroquinone in ethanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (DB-FFAP 123-3232E). The conversions of propylene, mass balance of carbon, yields of major products or byproducts such as acrylic acid, acrolein, acetaldehyde, propionaldehyde, propionic acid, acetic acid, $CO_x$ (CO and $CO_2$) are calculated using the formula below:

Iso-propanol conversion (%)=(moles of iso-propanol fed−moles of iso-propanol in R1-Exit)/moles of iso-propanol fed.

Carbon mass balance (%)=(total amount of carbon from molecules in R1-Exit including $CO_2$, CO, propylene, acetaldehyde, acrolein, acetic acid, propionic acid, acrylic acid)/(total amount of carbon from iso-propanol fed)*100

The yields of acrolein, acetaldehyde, and acrylic acid, and carbon mass balance after the $2^{nd}$ stage reactor were calculated using the formula below:

$$\text{Yield of product (\%)=(moles of the product in R2-Exit)/moles of iso-propanol fed*100}$$

The test was conducted with different $2^{nd}$ stage reactor temperatures while maintaining the temperature of 1st stage reactor constant, as shown in the reaction conditions in Table 3, which also includes the ratio of oxygen to iso-propanol (02/IPA). The results are listed in the Table 4. The mass balance of carbon was adjusted to 99% by adjusting the feed rate of iso-propanol. With almost complete conversion of iso-propanol, the yield of acrylic acid was above 70%. The yield of propionic acid was very low around 0.07% which led to the mass ratio of PA/AA around 0.0009.

TABLE 3

| | R1 Bath Temp (° C.) | R1 Peak Temp (° C.) | R2 Bath Temp (° C.) | R2 Peak Temp (° C.) | O$_2$/IPA |
|---|---|---|---|---|---|
| Ex. 3 | 305 | 397 | 270 | 272 | 1.67 |
| Ex. 4 | 305 | 397 | 300 | 312 | 2.05 |
| Ex. 5 | 305 | 397 | 310 | 317 | 2.05 |
| Ex. 6 | 305 | 397 | 320 | 329 | 2.05 |

TABLE 4

| | Product Yield (%) | | | | | | | | |
|---|---|---|---|---|---|---|---|---|---|
| | CO$_x$ | Fmd | Ald | Ace | PP | Acro | HAc | PA | AA |
| Ex. 3 | 6.97 | 1.28 | 1.76 | 3.44 | 3.71 | 33.8 | 3.07 | 0.059 | 45.1 |
| Ex. 4 | 10.2 | 0.97 | 0.35 | 2.60 | 3.78 | 6.27 | 4.6 | 0.103 | 70.9 |
| Ex. 5 | 10.2 | 0.97 | 0.30 | 2.66 | 4.24 | 4.96 | 5.43 | 0.066 | 71.3 |
| Ex. 6 | 12.5 | 0.68 | 0.23 | 2.04 | 4.01 | 3.70 | 5.73 | 0.069 | 70.3 |

Fmd = formaldehyde

IV. Comparative Example—Oxidation of 1-Propanol to Acrolein

Similar to Example 1, 1-propanol (Sigma Aldrich, >99.5% pure) was used instead of iso-propanol. The catalyst used in the first stage reactor is Mo- and Bi-based mixed oxide catalyst, abbreviated as R1 catalyst. In this example 10 ml of a Mo- and Bi-based R1 catalyst from Nippon Kayaku Co. (Tokyo, Japan) was loaded into a 1" outer diameter (OD) stainless steel (SS) first stage tube reactor heated in an electrical clam-shell furnace. The reactor was heated in flowing gas mixture of air 208.00 sccm and N2 38.2 sccm to the desired reactor temperature, then a mixture of liquid containing 1-propanol and D.I. was injected at rate of ~3.29 g/h iso-propanol and water ~0.92 g/h The product mixture out of the 1st stage reactor, abbreviated as R1-Exit, was collected and analyzed. The R1-Exit first flew through Trap 1 which was a 100-500 ml stainless vessel wrapped with ¼" (0.635 cm) copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4 hours. An inhibitor solution of 6-12 grams was injected to Trap 2, Trap 3A and 3B before sample collection to prevent polymer formation. Trap 2 collected very little material most times. 0.2 wt. % of hydroquinone in methanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (MXT-1701 from Restek). Alternatively the R1-Exit was sent to on-line analyzer in a heat traced ⅛" SS tube to have formaldehyde byproduct analyzed.

The conversions of propylene, mass balance of carbon, yields of major products or byproducts such as acrylic acid, acrolein, acetaldehyde, formaldehyde, propionic acid, acetic acid, CO$_x$ (CO and CO$_2$) are calculated using the formula below:

1-propanol conversion (%)=(moles of 1-propanol fed−moles of 1-propanol in R1-Exit)/moles of 1-propanol fed.

Carbon mass balance (%)=(total amount of carbon from molecules in R1-Exit including CO$_2$, CO, propylene, formaldehyde, acetaldehyde, acrolein, acetic acid, propionic acid, acrylic acid)/ (total amount of carbon from 1-propanol fed) *100.

The yields of acrolein, acetaldehyde, and acrylic acid, and carbon mass balance after the $2^{nd}$ stage reactor were calculated using the formula below:

Yield of product (%)=(moles of the product in R1-Exit)/moles of iso-propanol fed*100

The test was conducted with two similar reactor set temperatures (250 and 245-249° C.) in different time-on-stream. The results are listed in the Table 5. The yield of acrolein is less than 25%, which is much lower than using iso-propanol as feed. In addition, the yield of PA is much higher vs. yield of AA or combined yield of "acrolein and AA".

TABLE 5

| Bath T/Bed PT | Conv. | Carbon M.B. | Product yield (%) | | | | | | | |
|---|---|---|---|---|---|---|---|---|---|---|
| T(° C.) | (%) | (%) | CO + CO$_2$ | Ald | Fmd | PP | acrolein | HAc | PA | AA |
| 250/333-349 | 93.5 | 100.0 | 20.5 | 14.5 | 1.33 | 20.2 | 24.7 | 11.1 | 0.83 | 0.37 |
| 245-249/345-349 | 95.5 | 100.0 | 28.8 | 14.1 | 2.79 | 14.9 | 21.2 | 10.4 | 0.87 | 2.47 |

Note:

PT = peak temperature, M.B. = mass balance, Ald = acetaldehyde, Fmd = formaldehyde, PP = propylene, HAc = acetic acid, PA = propionic acid, AA = acrylic acid.

V. Comparative Example—Oxidation of 1-Propanol to Acrylic Acid

Similar to Example 2, 1-propanol was used to replace iso-propanol as feed to be oxidized to acrylic acid in two stages. First 1-propanol was oxidized mainly to acrolein in first-stage reactor, in this case a tubular reactor. The catalyst used in the first stage reactor is Mo- and Bi-based mixed oxide catalyst, abbreviated as R1 catalyst. In this example 10 ml of a Mo- and Bi-based R1 catalyst from Nippon Kayaku Co. (Tokyo, Japan) was mixed with 10 ml of 1/8" (0.32 cm) Denstone™ 57 beads (Saint-Gobain Norpro, Stow, OH), before being loaded into a 2.54 cm (1") outer diameter (OD) stainless steel (SS) first stage tube reactor (0.834" (2.11 cm) ID).

The product mixture out of the 1st stage reactor, abbreviated as R1-Exit, was sent the $2^{nd}$ stage reactor in 1/4" (0.635 cm) SS tube heated by electrical heating tape. The skin temperature was controlled around 170±10° C.

The $2^{nd}$-stage reactor contains Mo, V-based mixed oxide catalyst, abbreviated as R2 catalyst. In this example 10 ml of a Mo- and V-based commercial R2 catalyst was loaded into the feed inlet side of a U-shaped SS tube with 1/2" (1.27 cm) OD. The other internal space of the U-shaped tube was filled with Denstone™ beads. The U-shaped tube was put into a fluidized sand bath furnace with the catalyst bed section immersed in the sand bath. The air was used to fluidize the sand at flow rate of 3.3-3.5 SCFM (standard cubic feet per minute) (0.093-0.099 m³/min). The temperature difference in the bath was controlled no more than 3° C. by maintaining high air flow rate. The bath temperature was adjusted to achieve desired conversion of acrolein to acrylic acid. The effluent from the $2^{nd}$ stage reactor was designated as R2-Exit.

The first stage reactor tube was first heated to 250° C. or higher in a clam-shell electrical furnace in flowing gas mixture of air 208.00 sccm and N2 38.2 sccm. The second stage reactor was heated to 300° C. The values of all gas flow rates were under standard temperature (0° C.) and standard pressure (101.3 kPa) conditions. The 1-propanol was mixed D.I. water (78.1 wt % of iso-propanol) and injected into a SS mixer vessel at rate of 0.083 ml/min when the reactor reached the desired temperature. The SS mixer vessel was heated to 160-170° C. with the feed air/nitrogen carrying the vapor into the reactor.

The R2-Exit was collected and analyzed. The R2-Exit first flew through Trap 1 which was a 100-500 ml stainless vessel wrapped with 1/4" (0.635 cm) copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4 hours. An inhibitor solution of 6-12 grams was injected to Trap 2, Trap 3A and 3B before sample collection to prevent polymer formation. Trap 2 collected very little material most times. 0.2 wt. % of hydroquinone in methanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (MXT-1701 from Restek).

Alternatively the R2-Exit was sent to on-line analyzer in a heat traced 1/8" SS tube to have formaldehyde byproduct analyzed.

The conversions of propylene, mass balance of carbon, yields of major products or byproducts such as acrylic acid, acrolein, formaldehyde, acetaldehyde, propionic acid, acetic acid, $CO_x$ (CO and $CO_2$) are calculated using the formula below:

$$\text{1-propanol conversion (\%)} = (\text{moles of 1-propanol fed} - \text{moles of 1-propanol in R2-Exit})/\text{moles of 1-propanol fed}.$$

$$\text{Carbon mass balance (\%)} = (\text{total amount of carbon from molecules in R2-Exit including } CO_2, CO, \text{ propylene, formaldehyde, acetaldehyde, acrolein, acetic acid, propionic acid, acrylic acid})/(\text{total amount of carbon from 1-propanol fed}) * 100$$

The yields of acrolein, formaldehyde, acetaldehyde, and acrylic acid, and carbon mass balance after the $2^{nd}$ stage reactor were calculated using the formula below:

$$\text{Yield of product (\%)} = (\text{moles of the product in R2-Exit})/\text{moles of 1-propanol fed} * 100$$

The test was conducted with $2^{nd}$ stage reactor temperature set at 300° C. while changing the temperature of 1st stage reactor slightly. The results are listed in the Table 6. The mass balance of carbon was adjusted to 99% by adjusting acetic acid yield which may be affected by methanol added to the trap. With almost complete conversion of 1-propanol, the yield of acrylic acid was only 20.4% while PA yield was as high as 4.71%. The mass ratio of PA/AA is 0.225 which is way higher than 0.001 as shown in the product from iso-propanol as feed.

TABLE 6

| R1 ST/PT | R2 ST/PT | O2/1- | Product yield (%) | | | | | | | |
|---|---|---|---|---|---|---|---|---|---|---|
| (° C.) | (° C.) | PrOH | CO + CO2 | Fmd | Ald | PP | acrolein | HAc | PA | AA |
| 260/358-376 | 300/302 | 2.05 | 35.8 | 2.39 | 0.89 | 16.9 | 0.92 | 18.9 | 4.71 | 20.4 |

Note:

PT = peak temperature, IPA = iso-propanol, Fmd = formaldehyde, Ald = acetaldehyde, PP = propylene, HAc = acetic acid, PA = propionic acid, AA = acrylic acid.

We claim:

1. A method comprising:

selectively oxidizing iso-propanol over a first mixed metal oxide catalyst in the presence of oxygen in the vapor phase to produce a first product comprising acrolein wherein a mass ratio of propionic acid to acrolein is less than 0.002, and selectively oxidizing the first product over a second mixed metal oxide catalyst in the presence of oxygen in the vapor phase to produce a second product comprising acrylic acid, wherein the second mixed metal oxide catalyst has a different composition from the first mixed metal oxide catalyst;

wherein the first mixed metal oxide catalyst comprises oxides of molybdenum and bismuth, and wherein the second mixed metal oxide catalyst comprises oxides of molybdenum and vanadium.

2. The method according to claim 1, wherein the second mixed metal oxide catalyst further comprises at least one additional element selected from the group consisting of tungsten, copper, iron, antimony, and phosphorus.

3. The method according to claim 1, wherein the first mixed metal oxide catalyst further comprises at least one additional element selected from the group consisting of iron, cobalt, and nickel.

4. The method according to claim 1, wherein the oxygen is present in the form of purified oxygen, air, or lattice oxygen of the mixed metal oxide.

5. The method according to claim 1, wherein the iso-propanol is produced from biomass-derived feedstock.

6. The method according to claim 1, wherein the acrolein has a ratio of $^{14}C:^{12}C$ of at least $0.5 \times 10^{-13}$.

7. The method according to claim 1, wherein a mass ratio of propionic acid to acrylic acid is less than 0.001.

8. The method according to claim 1, wherein selectively oxidizing the iso-propanol occurs in the presence of steam.

9. The method according to claim 1, wherein selectively oxidizing the acrolein occurs in the presence of steam.

10. The method according to claim 1, further comprising recovering acrolein by one or more techniques selected from absorption using water or an organic solvent, extraction, fractional distillation, and melt crystallization.

11. The method according to claim 10, further comprising recovering acrylic acid by one or more techniques selected from absorption using water or an organic solvent, extraction, fractional distillation, and melt crystallization.

* * * * *